US011998472B2

(12) United States Patent
Sudell

(10) Patent No.: US 11,998,472 B2
(45) Date of Patent: *Jun. 4, 2024

(54) PORTABLE TRACTION DEVICE WITH SLING

(71) Applicant: THE NECK HAMMOCK, INC., Wilmington, DE (US)

(72) Inventor: Steven Sudell, Santa Monica, CA (US)

(73) Assignee: The Neck Hammock, Inc., Wilmington, DE (US)

( * ) Notice: Subject to any disclaimer, the term of this patent is extended or adjusted under 35 U.S.C. 154(b) by 826 days.

This patent is subject to a terminal disclaimer.

(21) Appl. No.: 17/080,829

(22) Filed: Oct. 26, 2020

(65) Prior Publication Data

US 2021/0038419 A1 Feb. 11, 2021

Related U.S. Application Data

(63) Continuation of application No. 15/879,881, filed on Jan. 25, 2018, now Pat. No. 10,813,784, which is a
(Continued)

(51) Int. Cl.
*A61F 5/00* (2006.01)
*A61F 5/048* (2006.01)
(Continued)

(52) U.S. Cl.
CPC .............. *A61F 5/048* (2013.01); *A61F 5/055* (2013.01); *A61H 1/005* (2013.01); *A61H 1/0296* (2013.01); *A61M 21/02* (2013.01); *A61H 23/02* (2013.01); *A61H 2201/0123* (2013.01); *A61H 2201/10* (2013.01); *A61H 2201/1284* (2013.01); *A61H 2201/1607* (2013.01);
(Continued)

(58) Field of Classification Search
USPC ....................................................... D24/191
See application file for complete search history.

(56) References Cited

U.S. PATENT DOCUMENTS 1,556,496 A 10/1925 Davis
2,674,996 A 4/1954 Averill et al.
(Continued)

FOREIGN PATENT DOCUMENTS

CN 214778 Y * 12/1992
CN 2403385 Y 11/2000
(Continued)

OTHER PUBLICATIONS

CN 2147788 Y Translation (Year: 1993).*
(Continued)

*Primary Examiner* — Kim M Lewis
(74) *Attorney, Agent, or Firm* — Workman Nydegger

(57) ABSTRACT

A portable traction device can include a sling that is sized to cradle a user's head. The sling can be associated with an anchor that is positioned a height above the floor when the portable traction device is in use. A tensile force vector between the anchor and the sling allows for cervical traction. The portable traction device can additionally include one or more flexible straps between the anchor and the sling that can differentially regulate the amplitude of the tensile force vector by stretching.

19 Claims, 13 Drawing Sheets

Related U.S. Application Data continuation-in-part of application No. 15/600,901, filed on May 22, 2017, now Pat. No. 10,813,785.

(60) Provisional application No. 62/374,259, filed on Aug. 12, 2016.

(51) Int. Cl.

| | |
|---|---|
| *A61F 5/055* | (2006.01) |
| *A61H 1/00* | (2006.01) |
| *A61H 1/02* | (2006.01) |
| *A61M 21/02* | (2006.01) |
| *A61H 23/02* | (2006.01) |
| *A61M 21/00* | (2006.01) |

(52) U.S. Cl.
CPC ............... *A61H 2201/1611* (2013.01); *A61H 2201/5005* (2013.01); *A61H 2201/5023* (2013.01); *A61M 2021/0027* (2013.01); *A61M 2205/502* (2013.01)

(56) References Cited

U.S. PATENT DOCUMENTS

| | | | |
|---|---|---|---|
| 3,033,198 A | 5/1962 | Jensen | |
| 3,118,443 A | 1/1964 | Dykinga | |
| 3,221,735 A * | 12/1965 | Goodman | A61H 1/0218 D24/188 |
| D213,478 S | 3/1969 | Nightingale | |
| 3,540,439 A * | 11/1970 | Gaylord, Jr. | A61H 1/0218 602/36 |
| 4,220,147 A | 9/1980 | Allen | |
| 5,010,880 A | 4/1991 | Lamb | |
| D332,495 S | 1/1993 | Lake | |
| 5,421,809 A | 6/1995 | Rise | |
| 5,451,202 A | 9/1995 | Miller et al. | |
| 5,479,667 A | 1/1996 | Nelson et al. | |
| D373,803 S | 9/1996 | Winans | |
| 5,908,206 A | 6/1999 | Lopresti, Jr. | |
| D422,710 S | 4/2000 | Maynard | |
| 6,113,564 A | 9/2000 | McGuire | |
| 6,183,501 B1 | 2/2001 | Latham | |
| 6,939,269 B2 | 9/2005 | Makofsky | |
| 7,033,333 B1 * | 4/2006 | Croft | A61F 5/04 602/17 |
| D550,847 S | 9/2007 | Kixmiller | |
| D626,244 S | 10/2010 | Sagnip et al. | |
| D631,924 S | 2/2011 | Baldwin | |
| D636,036 S | 4/2011 | Rios | |
| D654,124 S | 2/2012 | Davis | |
| D660,439 S | 5/2012 | Chen et al. | |
| 8,657,774 B1 | 2/2014 | Fisher | |
| 8,782,831 B2 | 7/2014 | Houston et al. | |
| D713,049 S | 9/2014 | Shah | |
| D713,535 S | 9/2014 | Chiang et al. | |
| 8,967,947 B2 | 3/2015 | Huss | |
| D726,262 S | 4/2015 | Linkjendal | |
| D742,461 S | 11/2015 | Baldwin | |
| D749,230 S | 2/2016 | Safko et al. | |
| 9,386,943 B2 | 7/2016 | Strickland et al. | |
| 9,420,905 B2 | 8/2016 | Willingham | |
| 9,498,675 B2 | 11/2016 | Walworth | |
| 9,526,965 B2 | 12/2016 | Gatherer | |
| 9,586,074 B2 | 3/2017 | Autogue | |
| 9,597,541 B2 | 3/2017 | Hinds et al. | |
| D784,546 S | 4/2017 | Gordon | |
| D789,546 S | 6/2017 | Matfus et al. | |
| D790,072 S | 6/2017 | Hiebert | |
| 9,668,906 B2 | 6/2017 | Thorgilsdottir et al. | |
| 9,713,546 B2 | 7/2017 | Thorsteinsdottir et al. | |
| D794,809 S | 8/2017 | Gramza et al. | |
| D812,236 S | 3/2018 | Burke et al. | |
| 9,930,882 B2 | 4/2018 | Owen | |
| D817,664 S | 5/2018 | Kim | |
| D824,035 S | 7/2018 | Sudell | |
| D845,492 S | 4/2019 | Sudell | |
| D845,493 S | 4/2019 | Sudell | |
| D845,494 S | 4/2019 | Sudell | |
| 10,307,284 B2 * | 6/2019 | Sudell | A61F 5/042 |
| D861,804 S | 10/2019 | Rios | |
| D870,898 S | 12/2019 | Sudell | |
| 10,813,784 B2 * | 10/2020 | Sudell | A61M 21/02 |
| 2005/0113728 A1 | 5/2005 | Heinz et al. | |
| 2006/0264302 A1 | 11/2006 | Sjodin | |
| 2006/0288490 A1 | 12/2006 | Mikkelsen et al. | |
| 2010/0222729 A1 | 9/2010 | Chin et al. | |
| 2012/0329620 A1 | 12/2012 | White et al. | |
| 2013/0005544 A1 | 1/2013 | Butler et al. | |
| 2014/0249461 A1 | 9/2014 | Bissell et al. | |
| 2018/0028389 A1 | 2/2018 | Adimari | |
| 2018/0042757 A1 | 2/2018 | Sudell | |
| 2018/0161192 A1 | 6/2018 | Sudell | |

FOREIGN PATENT DOCUMENTS

| | | |
|---|---|---|
| CN | 101815559 A | 8/2010 |
| GB | 1315519 A | 5/1973 |
| JP | 2000-342613 A | 12/2000 |
| JP | 2004-049824 A | 2/2004 |
| WO | WO 8700386 A1 * | 7/1986 |

OTHER PUBLICATIONS

WO 8700386 A1 Tramnslation (Year: 1986).*
Amazon, The Neck Hammock 2.0, reviewed Apr. 2018 [online], [site visited Oct. 4, 2018]. Available from Internet, <URL: https://www.amazon.com/Nech-Hammock-2-0-Original-Relaxation/dp/B07FX5CXKC/ref=cm_cr_arp_d_product_top?ie=UTF8>.
International Search Report and Written Opinion issued in PCT/US2018/015415 dated Mar. 22, 2018.
Selenechen Hammock for Neck, Neck Massager for Men Women, Relaxation Massager Great for Neck Pain Relief Amazon.
U.S. Patent Application filed on Nov. 26, 2019m by Steven Sudell, U.S. Appl. No. 29/714,894.
YouTube The Neck Hammock, announced Nov. 28, 2017, [online], [site visited Oct. 4, 2018], Available from Internet, <URL: https://www.youtube.com/watch?v=CdpecklmCCw>.

\* cited by examiner

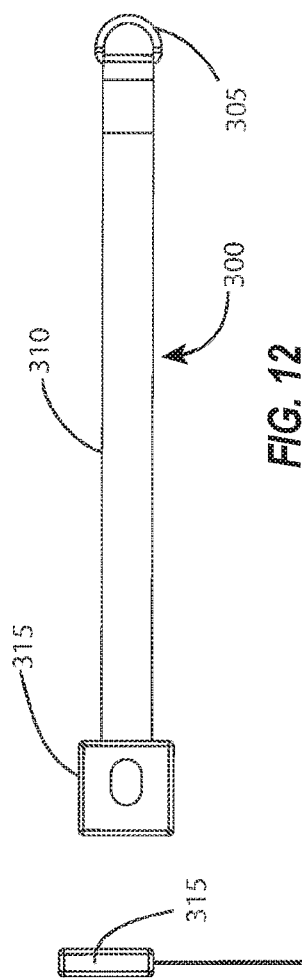
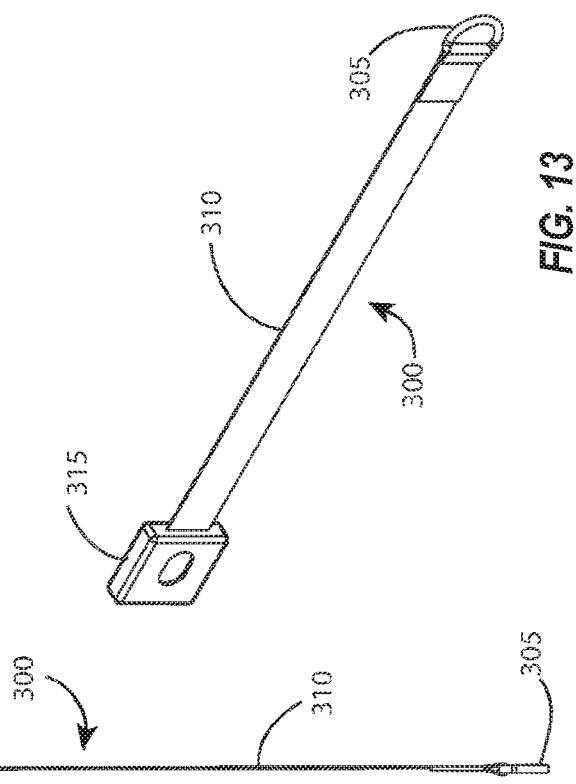
FIG. 12
FIG. 13
FIG. 14

PORTABLE TRACTION DEVICE WITH SLING

CROSS-REFERENCE TO RELATED APPLICATIONS

This application is a continuation of U.S. patent application Ser. No. 15/879,881, filed Jan. 25, 2018, now U.S. Pat. No. 10,813,784 issued on Oct. 27, 2020, which is a continuation-in-part of U.S. patent application Ser. No. 15/600,901 filed May 22, 2017, now U.S. Pat. No. 10,813,785 issued on Oct. 27, 2020, which claims priority to and the benefit of U.S. Provisional Application No. 62/374,259 filed Aug. 12, 2016. The foregoing are incorporated herein by reference in their entirety.

BACKGROUND

Technical Field

This invention relates generally to cervical traction, and, more particularly, to a portable device to apply cervical traction.

Background and Relevant Art

Cervical traction is a method of applying force to relieve neck pain for individuals suffering from neck arthritis, a herniated/bulging disc in the neck, pinched nerves, neck strains and cervical muscle spasms. Cervical traction entails urging the head away from the neck. Doing so gradually stretches muscles and ligaments around the vertebrae of the spine and expands space between vertebrae. Pinched nerves are released. Herniated and bulging discs relax as pressure is relieved. Blood circulation improves to the structures of the cervical spine, helping to oxygenate muscles, nerves, tendons, and ligaments.

In the past, individuals were relegated to visiting a physical therapist for cervical traction. Such visits are time consuming, often inconvenient, and costly. Additionally, patients can afford such visits only periodically.

Today, some home cervical traction devices are available. Such devices, however, are complex, cumbersome, bulky, costly, and potentially injurious. As one example, many home traction devices include headgear which include straps around the user's forehead, head, and chin. Such headgear is not only cumbersome, constricting, and inconvenient, but may also exert stresses at the jaw that may lead to or exacerbate temporomandibular disorders. As another example, many such devices require weights and pulleys to exert tension. Such devices are bulky, cumbersome, and inconvenient.

Also, many devices include clamps and brackets for attachment to doors and furniture. Such hardware mars surface finishes and interferes with use of the door or furniture. For example, some devices require hardware that attaches the device to a door frame. The hardware prevents the door from being able to close and may damage the surface finish of the frame, or even make dents. Likewise, securing these devices to other household features, such as railings or entryways, can block passageways or otherwise obstruct individuals and mar surface finishes. Accordingly, there are a number of disadvantages and improvements to be made to cervical traction devices that can be addressed.

SUMMARY

Technical Problem

As noted above, current devices fail to overcome a number of technical problems in the field of cervical traction, creating a need for an easy to use, compact, non-marring, effective traction device that minimizes discomfort and avoids potentially injurious stresses. The technical problems that need to be overcome include devices that are complex, cumbersome, bulky, costly, and potentially injurious.

Devices that include headgear, such as straps that put pressure on a user's forehead or chin are uncomfortable, cumbersome, and create a risk of injury to the user's jaw or exacerbate temporomandibular disorders. Also, devices that include weights and pullies are complex to set up and difficult to adjust depending on user-specific needs. For example, some users may require larger traction forces than others for proper cervical traction. Adjusting the height, size, and traction forces of these devices may be complex, time consuming, and require the user to store multiple weights and reconfigure the device before each use.

Another technical problem, which is not solved with current devices, includes device installation that mars the surface finishes of doors and furniture. Current devices interfere with the use of furniture and doors as described above. Devices designed to attach to door frames, for example, may prevent the door from properly closing. Therefore, to use these devices without permanently interfering with a door, or other household feature, requires the user to install and uninstall the devices with each use. This leads to further damage and marring of surface finishes.

Additionally, current devices may not provide enough additional blood-flow to the cervical area of a user to fully oxygenate and revitalize the cervical muscles when used for a short period of time. Thus, users are required to spend long periods of time using inefficient traction devices, which may be inconvenient or boring. Furthermore, a user must relax to effectively loosen the cervical muscles. Users may often desire to listen to music to relax but may find it uncomfortable to wear headphones while using current traction devices, since the current traction devices push conventional headphones painfully against the ears of the user while using the traction device.

Solution to Problem

To solve one or more of the problems set forth above, a portable traction device according to principles of the invention may include an elongated sling having a first side, a second side opposite the first side, a superior edge, and an inferior edge. The sling can be made of a flexible material and sized and shaped to cradle an occipital bone portion of a user's head between the superior edge and the inferior edge of the sling as the first side extends to a first side of the user's head and the second side extends to a second side of the user's head. A frictional portion of the sling frictionally engages the occipital bone portion of the user's head. The frictional portion, according an embodiment of the portable traction device described herein, can include, for example, the total surface area of the sling that contacts the user's head during use. This frictional portion provides enough friction between the sling and the head of a user to pull on the user's head and sufficiently stretch the cervical muscles without the need for added chin or forehead straps. Thus, portable traction devices of the present disclosure reduce stresses to the jaw of the user and decrease the risk of exacerbating temporomandibular disorders while efficiently and effectively providing therapeutic cervical traction.

Portable traction devices disclosed herein can additionally include a pair of side attachments, including a first side attachment and a second side attachment, that extend from the first side of the sling and the second side of the sling, respectively, and a pair of flexible elastic tethers (e.g., shock cords) configured to attach to the pair of side attachments. Each flexible elastic tether includes a proximal end and a distal end. The proximal end of a first tether is configured to attach to the first side attachment of the sling, and the proximal end of the second tether is configured to attach to the second side attachment of the sling. The distal ends of the first and second tethers are configured to attach to an anchor that is selectively attachable to an anchoring object at a height above the floor while the portable traction device is in use. Portable traction devices of the present disclosure enable simple and easy use, reducing installation time and complexity and eliminating the need to store multiple weights or other cumbersome components.

The portable traction devices disclosed herein provide additional benefits over current devices. For example, during use, the flexible elastic tethers associated with the sling are strained and at an acute angle relative to the floor. These strained flexible elastic tethers produce a tensile force on the user's head that includes a vector component parallel to the floor and towards the anchor, and a vector component perpendicular to the floor and upward, away from the floor. The tensile force of the elastic tethers can easily and quickly be adjusted without added components or device reconfiguration. For example, if a user needs added tensile force applied for proper or more comfortable cervical traction, the user simply positions her head further away from the door, using the same elastic tethers. Likewise, the angle of the force can simply and quickly be adjusted by changing the position/height of the anchor above the ground. The vertical component of the tensile force is sufficient to retain the user's head within the sling, while simultaneously providing enough horizontal traction force, without the need for forehead or chinstraps. In other words, the vertical component of the tensile force can act as a normal force to increase friction between the user's head and the sling. This friction between the user's head and the sling is sufficient to hold the user's head in the sling while the horizontal component of the tensile force produces cervical traction of the user's neck. Thus, as discussed above, the present invention reduces user discomfort and potential injury by eliminating extra chin and forehead straps, and reducing the complexity of the device, making it easier and substantially faster to set up, use, and disassemble—all of which significantly increase the portability of the disclosed portable traction devices.

In one embodiment of the invention, the sling includes various layers. A first and third layer can include flexible fabric, and a second layer can be structural, having a flexible cushioning material. The various layers can provide comfort and durability while simultaneously conforming to the curves and contours of a user's head to provide enough friction, thereby removing the need for chin/forehead straps, as discussed above. The multiple layers may also allow space therebetween for securing various electronic components, such as wires, speakers, resonant actuators, and/or control modules without causing discomfort to the user. Essentially, the various layers can enable the incorporation of such components into the sling without sacrificing the comfort or the aforementioned improvements to efficiency and effectiveness of the portable traction devices disclosed herein.

The sling can additionally include one or more speakers for the user to enjoy relaxing music without the need to wear traditional headphones, which can be uncomfortable while using the traction device of the present disclosure. A control module can also be included to allow the user to adjust the volume or song being played through the speakers.

The sling can additionally include one or more resonant actuators that correspond in position to the user's cervical muscles. The user can control a vibrational intensity or frequency of the resonant actuator to loosen and/or massage the user's cervical muscles. The vibrations of the resonant actuator can promote additional blood-flow and oxygenation to the muscles, increasing the effectiveness of the traction device and reducing the amount of time needed to obtain desired results.

Portable traction devices of the present disclosure can include a sling having an arcuate superior edge that extends up the back of a user's head, providing additional surface area and enlarging the frictional portion of the sling to obviate chin straps and forehead straps. Thus, the arcuate edge is an improvement upon current devices as it can, for example, further reduce discomfort and risk of injury.

In one or more embodiments, the traction device of the present disclosure can include a quick-release connection between one or more elastic tethers. The quick release connection allows a user to quickly configure the traction device for use and eliminates the extra straps, cords, or other components. Additionally, the anchor may be configured to be left on an anchoring object during non-use so that the user does not have to re-configure the anchor for every use, and the anchor may have an unobtrusive footprint, allowing the furniture or other structure to which it is associated to substantially maintain its full utility and without greatly detracting from the aesthetic appeal thereof.

In one or more embodiments, the traction device includes multi-strand elastic cords that are generally planar and have a width. The multi-strand elastic cords can be secured to a sling, either removably or permanently, so that the multi-strand cords evenly distribute the tensile force throughout the width thereof. This distributed force is transferred to the sling and results in a more comfortable user experience, eliminating uncomfortable force concentrations or force unevenness within the sling. Multi-strand elastic cords may additionally increase the efficiency of cervical traction provided by portable traction devices incorporating the same.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which:

FIG. 12 illustrates a plan view of an exemplary anchor for a traction device according to principles of the invention;

FIG. 13 illustrates a top perspective view of the exemplary anchor of FIG. 12;

FIG. 14 illustrates a side elevation view of the anchor of FIG. 12;

DETAILED DESCRIPTION

Figure 1:
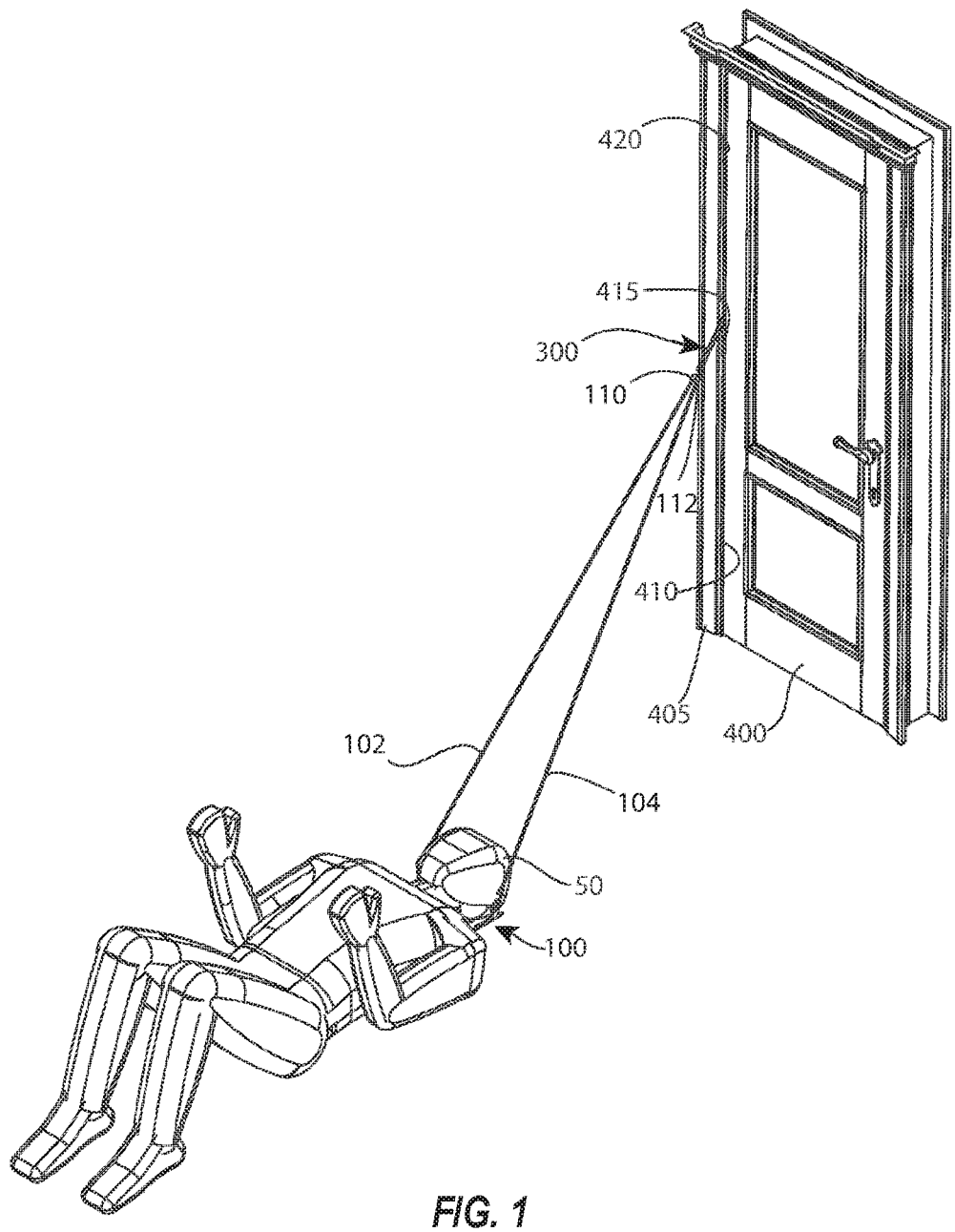
FIG. 1 illustrates a top perspective view of a traction device in use according to principles of the invention.

Before describing various embodiments of the present disclosure in detail, it is to be understood that this disclosure is not limited to the parameters of the particularly exemplified systems, methods, apparatus, products, kits, and/or processes, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, the terminology used herein is for the purpose of describing the embodiments, and is not necessarily intended to limit the scope of the claimed invention.

A portable traction device according to principles of the invention provides an easy to use, compact, non-marring, effective cervical traction device that minimizes discomfort during use and avoids potentially injurious stresses. A sling cradles a user's head, particularly the occipital bone portion of the user's head situated at the back and lower part of the skull. The sling includes cushions, which provide comfort but also enhance frictional engagement of the user's head. The sling also includes an arched portion. The arched portion enlarges the frictional portion of the sling, which includes the total surface area of the sling that is in contact with the user's head during use. For example, the sling, including an arched portion, extends beyond the occipital bone portion of the user's head to the lambdoid suture and lateral portion of the parietal bones of the user's head. The sling is attached to one end of each of a pair of flexible elastic tethers (e.g., shock cords). The other end of each of the pair of flexible elastic tethers is anchored to a fixed or immovable object (e.g., an anchoring object).

For example, the flexible cords can be anchored by a closed door (e.g., the hinged side of the door) between the door and door frame and preferably at a height near the middle of the door. Tension exerted by the flexible elastic tethers (e.g., shock cords) is directed from the cradled portion of the user's head to the anchoring object, at an acute angle relative to a horizontal floor surface. Thus, the tensile force vector applied at the sling includes a horizontal component away from the user's head and towards the anchoring object (e.g., the door) and a vertical component upwardly away from the floor. The vertical component helps to ensure that the sling does not slip off and disengage the user's head while the horizontal component of the tensile force vector provides cervical traction. In other words, the vertical component of the tensile force acts as a normal force to increase friction between the user's head and the sling. This friction between the user's head and the sling is sufficient to hold the user's head in the sling while the horizontal component of the tensile force produces cervical traction of the user's neck. It should be appreciated that he invention is not limited to attachment or anchoring to a door. Other elevated structures such as furniture, including table legs, banisters, or railings may be used as anchoring objects.

Figure 2:
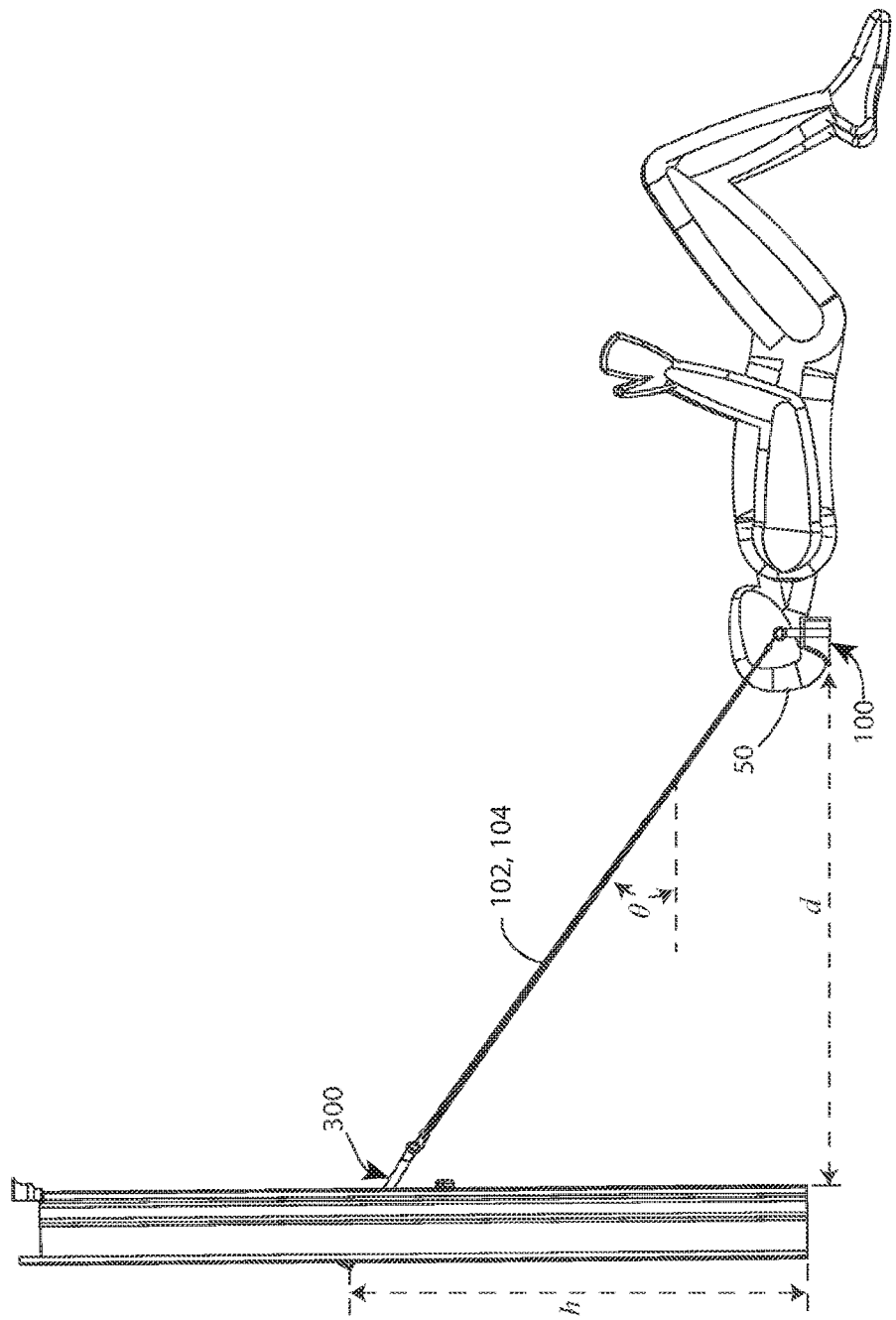
FIG. 2 illustrates a side elevation view of the traction device of FIG. 1 in use.
Figure 3:
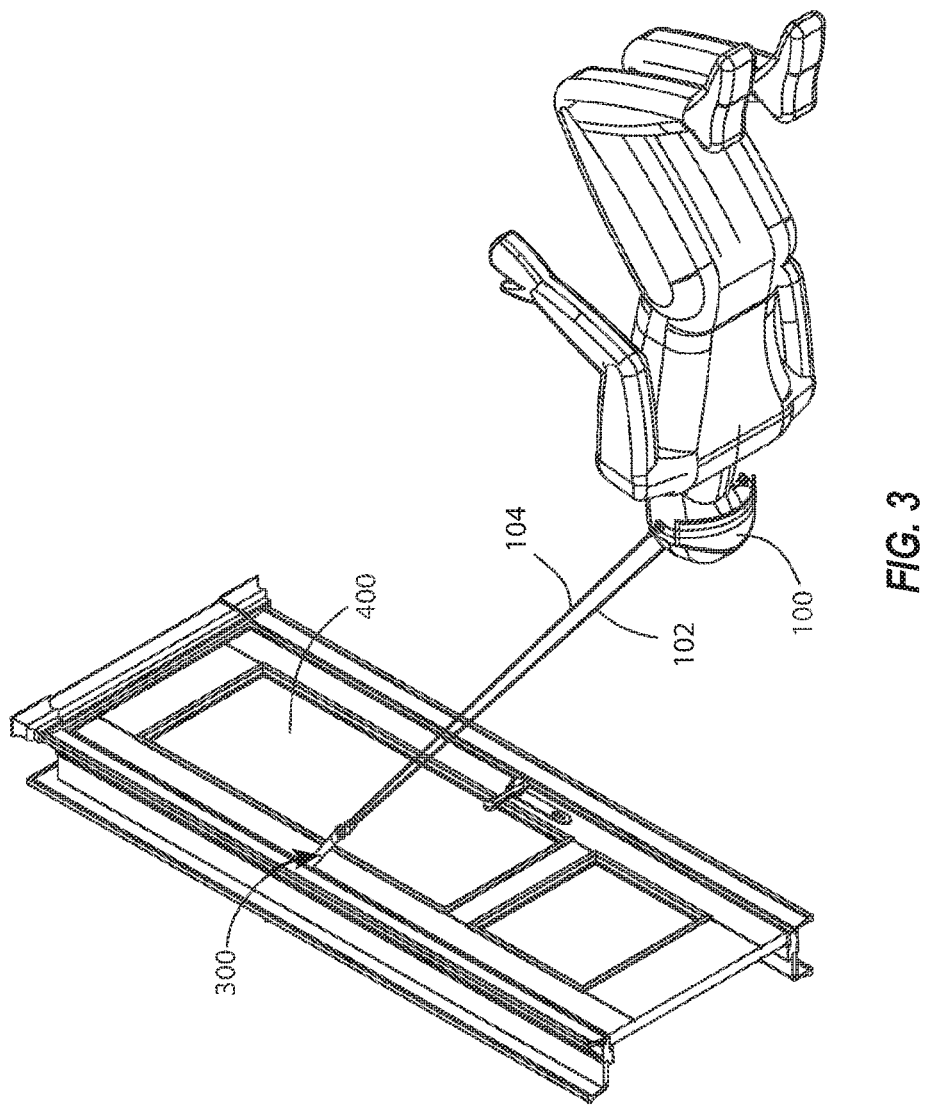
FIG. 3 illustrates a bottom perspective view of the traction device of FIG. 1 in use.

Referring now to the Figures, an exemplary use of a portable traction device, as described herein, is shown in FIGS. 1-3. A sling 100 cradles a user's head 50, particularly the occipital bone portion of the user's head situated at the back and lower part of the skull. In a preferred embodiment, the sling 100 extends beyond the occipital bone portion of the user's head, over the lambdoid suture, and extends to the lateral portion of the parietal bones of the user's head. Each of a plurality (e.g., an even number) of flexible elastic tethers 102, 104 (e.g., shock cords) is attached at a proximal end 106, 108 to the sling 100, and at the opposite, distal end 110, 112 to an anchor 300, where the ends 110, 112 converge. The anchor 300 is locked between the hinged edge of the door 400 and the door frame 405 when the door 400 is closed. In the depicted embodiment, the closed door 400 is an anchoring object, as that term is understood herein, while the sling 100 is in use.

With reference to FIG. 2, net tension exerted by the flexible elastic tethers 102, 104 is directed from the cradled portion of the user's head 50 to the anchor 300, at an acute angle θ (greater than 0° but less than 90°, preferably between 15° and 60°) relative to a planar (e.g., horizontal floor) surface. Thus, the tensile force vector on the sling that is created by the flexible elastic tethers 102, 104 includes a horizontal component away from the user's head 50 and towards the door 400, and a vertical component upwardly away from the floor. The vertical component of the tensile force vector helps to ensure that the sling 100 does not slip off and disengage the user's head. The vertical component of the tensile force vector provides a normal force that produces friction between the user's head and the sling 100. This friction obviates the need for a chin strap or other cumbersome head attachment while still providing a force necessary for cervical traction. In other words, a portion of the sling 100 that cradles the user's head 50, particularly at the occipital bone portion of the user's head situated at the back and lower part of the skull, is a frictionally engaging portion that does not slide off during normal use due to the horizontal component of the tensile force. Thus, during normal use, the sling 100 will not slide out from beneath the user's head 50. The angle θ and horizontal and vertical components of the force vector may be varied by adjusting d, the distance from the door, and h, the height of the anchor.

While the Figures may illustrate the user's head 50 against (or nearly against) the floor, it is understood that the vertical component of the tensile force vector may pull the user's head 50 upward from the floor. Such lifting of the user's head 50 provides considerable comfort to the user without appreciably compromising the horizontal component of the tensile force. A user may counteract the lifting force by urging his or her head against the floor. However, such counteraction is often unnecessary.

In the bottom-up perspective view of FIG. 3, the sling 100 relative to the head 50 is more clearly illustrated. The sling 100 cradles the user's head 50, particularly the occipital bone portion of the user's head situated at the back and lower part of the skull. The sling 100 extends beyond the occipital bone portion of the user's head to the lambdoid suture and lateral portion of the parietal bones of the user's head, thus enlarging the frictional portion as described above.

While the illustrated door 400 includes three hinges 410, 415, 420 with the anchor 300 above the intermediate hinge 415, the invention is not limited to such a configuration. Rather, the invention may be used with doors having fewer or more hinges. Even without an intermediate hinge 415, the anchor 300 may be frictionally secured (e.g., clamped) between the door 400 and frame 405 at a height above the bottom of the door. A user may adjust the vertical and horizontal components of the tensile force by adjusting the height at which the anchor 300 is disposed above the bottom of the door. This is because the horizontal and vertical components of the tensile force depend on the angle θ, which depends on the height above the bottom of the door. Structures other than a door may be used for anchoring in accordance with principles of the invention.

Figure 4:
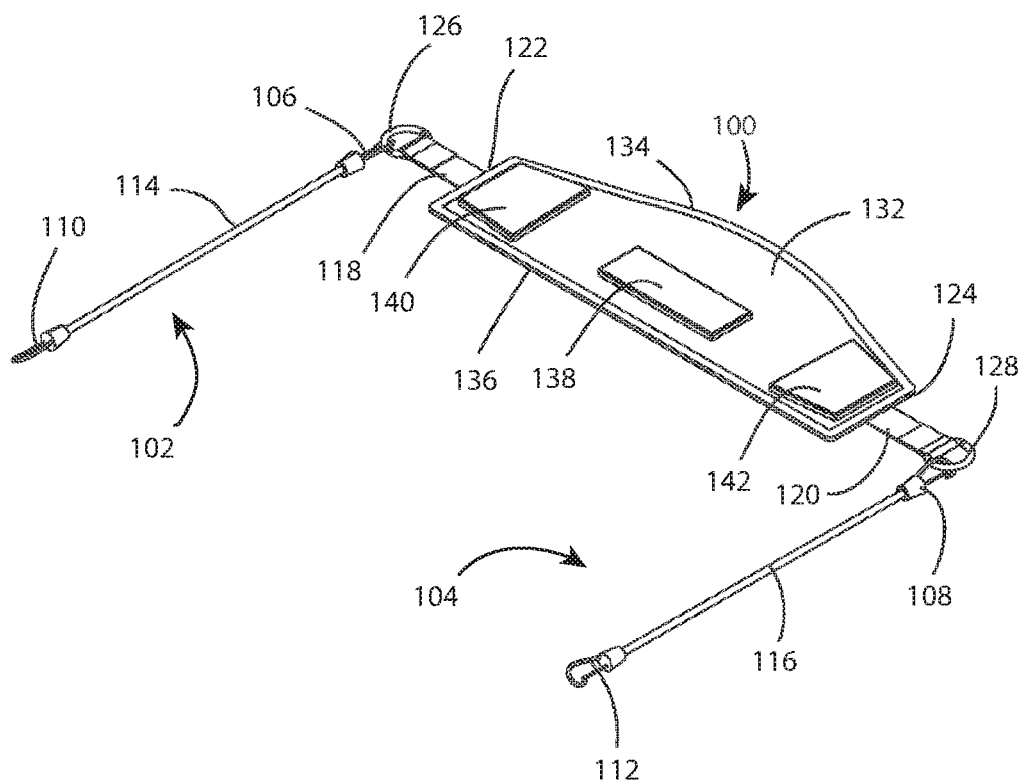
FIG. 4 illustrates a top perspective view of a sling for a traction device according to principles of the invention.
Figure 5:
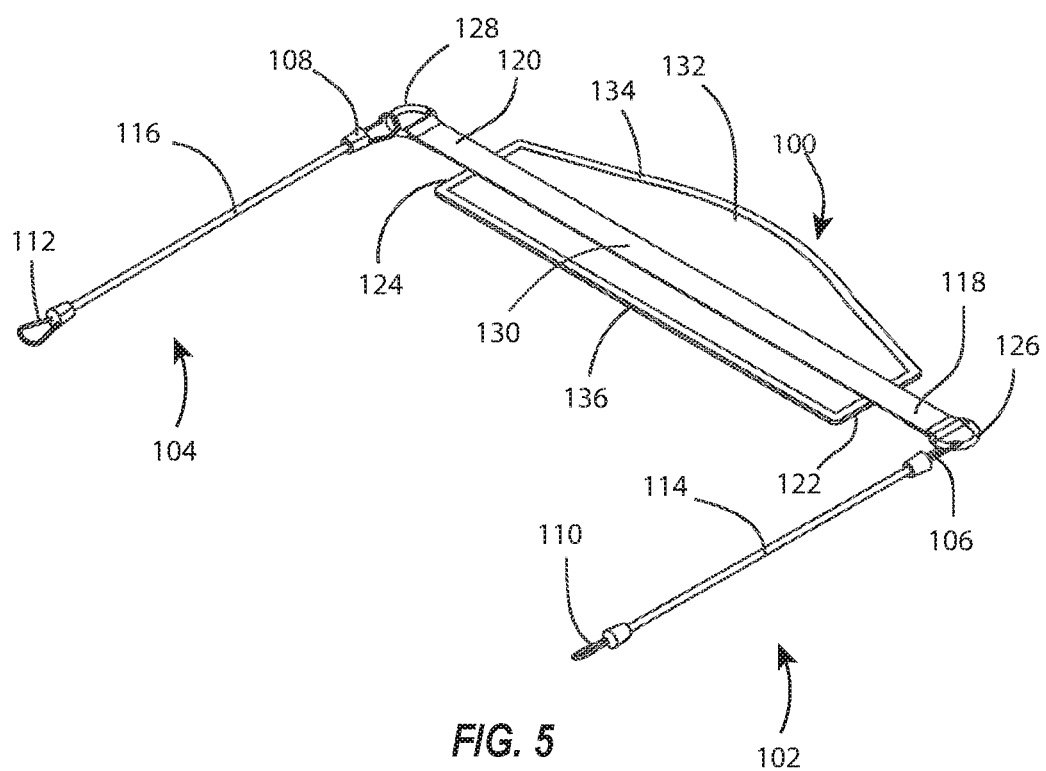
FIG. 5 illustrates a bottom perspective view of the sling of FIG. 4.

Referring now to FIGS. 4 and 5, the sling 100 and flexible elastic tethers (e.g., shock cords) 102, 104 are more clearly shown. Each flexible elastic tether 102, 104 includes an elastic cord 114, 116 composed of one or more elastic strands forming a core, covered in a woven sheath. While the sheath does not extend elastically, its strands spiral around the core so that a longitudinal pull causes it to squeeze the core, transmitting the core's elastic compression to the longitudinal extension of the sheath and cord. Elastic cords other than sheathed shock cords may be utilized without departing from the scope of the invention. Non-limiting examples include elastic straps such as EPDM and natural rubber tarp straps equipped with S-hooks at each end.

The flexible elastic tethers 102, 104 or other elastic cords exert a tension when stretched. The tensile force is preferably at least 5 lbs. for cervical traction, more preferably 10 to 30 pounds, and up to 5% to 10% of the user's body weight. A plurality of flexible elastic tethers (e.g., 2, 4, 6 or 8 shock cords) may be used to achieve a desired tensile force. Additionally, tension is a function of the strain (i.e., $\Delta L/L$, where L is the original length and $\Delta L$ is the elongation) of the flexible elastic tether 102, 104 or elastic cord 114, 116, with tension increasing with increasing strain. Thus, tensile force may be adjusted by adjusting the strain.

Each flexible elastic tether 102, 104 includes a metal or plastic hook attached to each proximal end 106, 108 and each distal end 110, 112 of the flexible elastic tethers 102, 104. The hooks may be opened or closed and/or selectively opened or closed. Attachments other than hooks, such as shackles, carabiners and straps may be utilized, at either or both ends of each flexible elastic tether to guard against unintentional disengagement of the flexible elastic tether.

A pair of flexible straps 118, 120 extend from opposite side edges 122, 124 of the sling. A nonlimiting example of a suitable flexible strap 118, 120 is nylon webbing. Attachments, such as D-rings 126, 128 are attached to the free ends of the strap ends 118, 120. Flexible elastic tethers 102, 104 connect to the attachments, i.e., to the D-rings 126, 128. As shown in FIG. 5, the strap ends 118, 120 may be opposite ends of strap 130 that extends across the bottom of sling 100. The strap 130 may be permanently or removably attached to the sling, such as with stitching, hook and loop fasteners, or belt loops.

The base 132 of the sling 100 includes a superior edge 134 with an arched (convex) section, an opposite inferior edge 136, and opposite side edges 122, 124. The base 132 is substantially planar. It may be comprised of any flexible fabric, including natural or synthetic fiber fabrics, that is comfortable, strong and durable. Nylon webbing, ballistic nylon fabric, nylon pack cloth, nylon canvass are non-limiting examples.

A plurality of cushions 138, 140, and 142 are provided for comfort at all pressure points. While three cushions are illustrated, one large cushion or several separate cushions may be used. Base cushion 138 is positioned where the occipital bone portion of the user's head will be located during normal use. Side cushions 140, 142 are positioned to cushion the sides of a user's head, below and/or over the ears, where the lambdoid suture and lateral portions of the parietal bones of the user's head are located. The cushions may provide comfort to the user as well as ensure proper alignment of the user's head within the sling 100.

An alternative embodiment of a sling 200 is shown in FIGS. 6-10. In this embodiment, the sling 200 may include a base 232, a plurality of cushions 238, 240, 242, and attachment members 226, 228 similar to other embodiments of a sling described herein. As can be seen from FIG. 6, the cushions 238, 240, 242 vary in size and shape from one location on the base 232 to another. For example, the base cushion 238 may include a curved edge 239 to accommodate the curved shape of a user's head, specifically a user's occipital bone, and provide added comfort to the user.

In general, the base cushion 238, as well as side cushions 240, 242, may be shaped so as to provide sufficient friction between the curved shape of a user's head and the sling 200 while the portable traction device is in use. As described above, the friction between the sling 200 and the head of a user provides the force necessary for cervical traction without the need for added headgear. Such headgear may include chinstraps or other cumbersome and uncomfortable headgear that causes discomfort and/or injury to the jaw or neck of the user.

Figure 6:
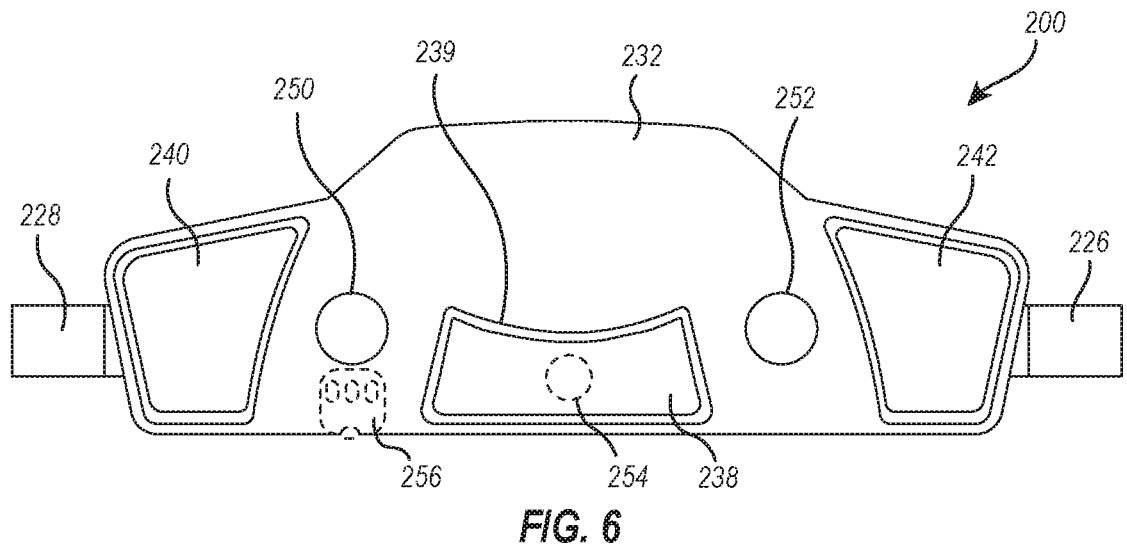
FIG. 6 illustrates a top plan view of another sling for a traction device according to principles of the invention.

FIG. 6 further illustrates an embodiment of a sling 200 that includes one or more speakers 250, 252 integrated into the base 232. The illustrated embodiment includes two speakers 250, 252. However, it will be appreciated that other embodiments may include more or less than two speakers integrated into the base 232 at various positions. FIG. 6 illustrates circular speakers 250, 252 for illustrative purposes, but the speakers may also vary in size and shape. In the illustrated embodiment, the speakers 250, 252 are disposed within the sling 200 to correspond in position with the ears of a user while the portable traction device is in use.

Thus, the speakers 250, 252 may be positioned between the base cushion 238 and respective first and second side cushions 240, 242.

Additionally, the embodiment illustrated in FIG. 6 may include a resonant actuator 254 for vibrating and massaging the cervical neck area of the user while the portable traction device is in use. The resonant actuator 254 may be integrated into the sling 200 to correspond in position with the cervical muscles of the user. The vibrations produced by the resonant actuator 254 increase blood flow and oxygenation to the user's cervical muscles, as well as aid in loosening and stretching the cervical muscles of the user. In the illustrated embodiment, the resonant actuator 254 is disposed centrally with the base cushion 238 of the sling 200. The resonant actuator 254 is illustrated with dotted lines to show the position of the actuator 254, which may be disposed underneath the base cushion 238. Other embodiments of the base assembly 200 may include more than one resonant actuator 254 positioned at various locations within the assembly 200.

One will appreciate that these other resonant actuator locations may correspond to other areas of the user's head and neck, which may be beneficial to massage through vibrations of the various resonant actuators for reasons stated above. Other beneficial positions of resonant actuators 254 may be clear to those of ordinary skill in the art. It is also noted that other embodiments of the sling 200, which are not illustrated herein, may include one or more resonant actuators 254 of various sizes, shapes, and vibrational capacities.

The embodiment illustrated in FIG. 6 may further include a control module 256 integrated into the base 132 of the sling 200 to enable the user to adjust and/or control the one or more speakers 250, 252 and the one or more resonant actuators 254 described above. The control module 256 is represented in dotted lines in FIG. 6 to show the position of the control module 256 within the assembly. However, in the illustrated embodiment, the control module 256 may not be accessible to the user through the front side of the sling shown in FIG. 6. It may, however, be accessible through the back side of the sling 200, as shown in FIG. 8.

The control module 256 may be positioned anywhere within the sling 200 so long as the control module 256 is easily accessible to the user while the traction device is in use. The control module may be wired to the various other components of the sling, such as the speakers 250, 252 and resonant actuator 254. The control module 256 may include a plurality of buttons or other control knobs, capacitive touch technology, or other user interface components that allow a user to control or adjust the speakers 250, 252 and resonant actuator 254. For example, the control module may include buttons that a user can push to adjust the volume of the speakers 250, 252. Also, for example, the user may be able to adjust the intensity of the vibrations produced by the resonant actuator 254.

In one embodiment, the control module 256 may digitally store a user's musical playlist or a plurality of preloaded relaxing sounds and/or songs provided by the manufacturer. In such an embodiment, the control module may also comprise one or more input ports, such as a USB port, to which a user may connect a digital storage device and upload songs to the control module 256.

Figure 7:
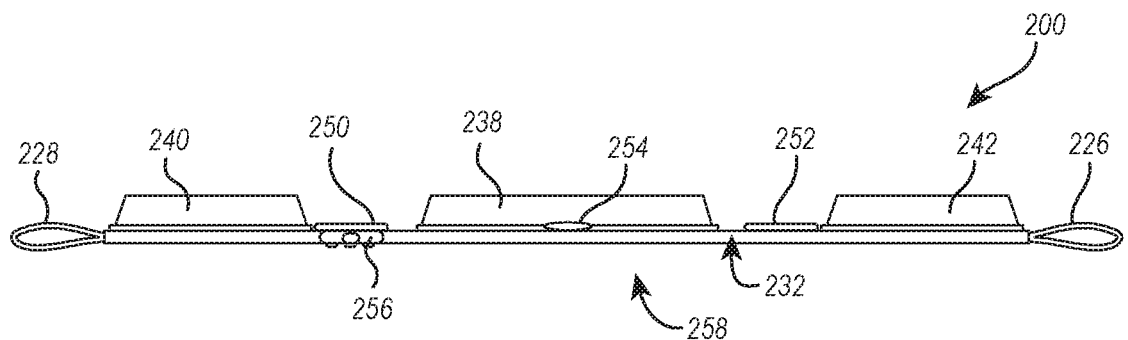
FIG. 7 illustrates a side elevation view of the sling of FIG. 6.
Figure 8:
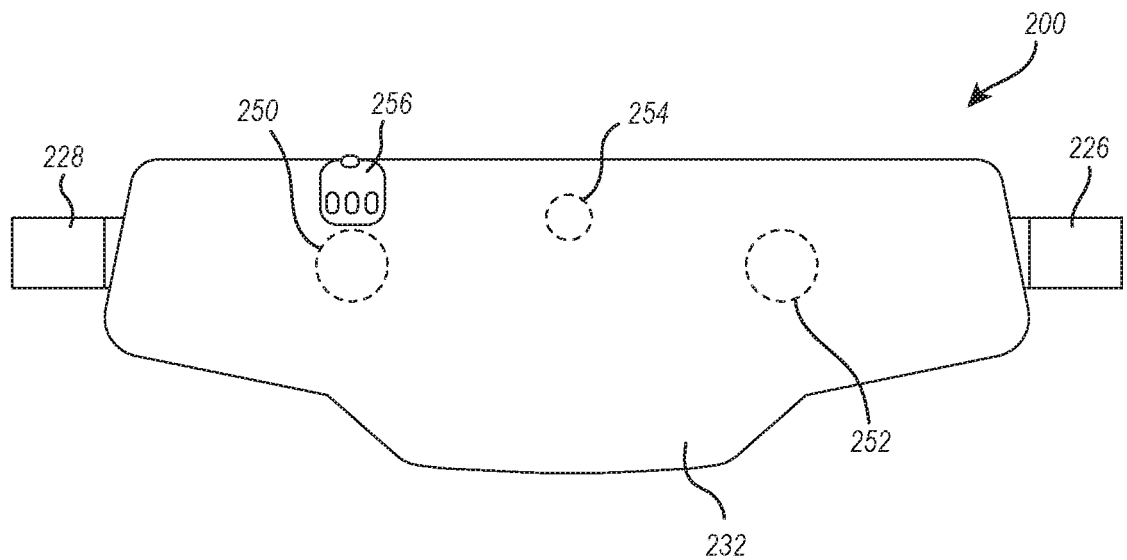
FIG. 8 illustrates a bottom plan view of the sling of FIG. 6.

Turning now to FIG. 7, a side view of the embodiment of the sling 200 illustrated in FIGS. 6 and 8 is shown. FIG. 7 illustrates positions of the speakers 250, 252, resonant actuator 254, and control module 256 described herein. For example, in the illustrated embodiment, the speakers 250, 252 may be disposed on the front side of the base 232 that is in contact with the user's head during use. The resonant actuator 254 may be disposed between layers of the base 232 and underneath the base cushion 238. The control module 256 may be substantially disposed between various layers of the base 232 with various buttons or other portions of the control module extending through the layers and beyond the back side 258 of the sling 200.

Figure 9:
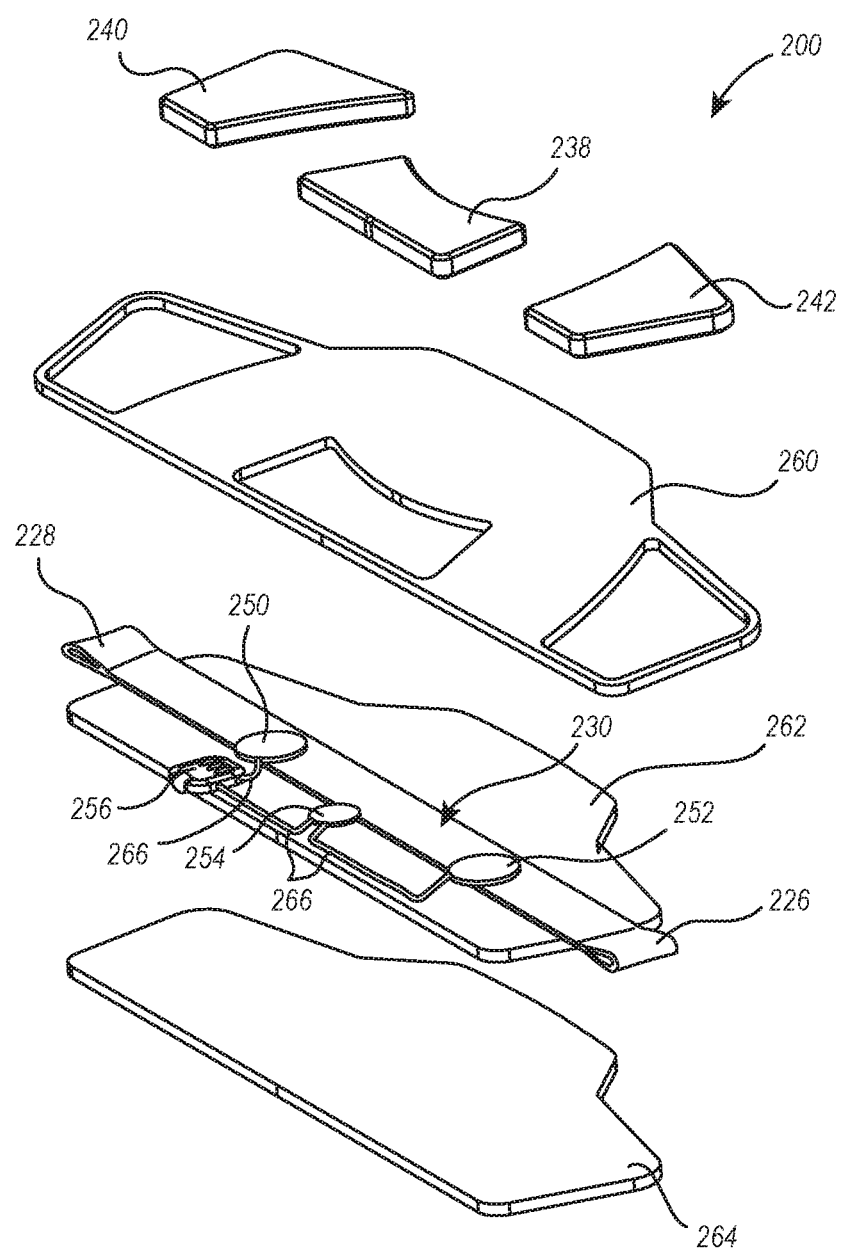
FIG. 9 illustrates an exploded perspective view of the sling of FIG. 6.

As alluded to above, the base 232 may include a plurality of layers. FIG. 9 illustrates an exploded view of the sling 200 illustrated in FIGS. 6-8. As shown, the sling 200 may include three layers. An inner first layer 260, a second layer 262, and an exterior third layer 264. The first 260 and third 264 layers may include or consist of a flexible, durable fabric. The second layer 262 may be a structural layer consisting of a flexible cushioning material. Some embodiments of the sling 200 may also include less than three layers or more than three layers.

As seen in FIG. 9, the various components of the sling 200, including cushions 238, 240, 242, speakers 250, 252, resonant actuator 254, strap 230, and control module 256 may be disposed between one or more of the three layers 260, 262, 264. For example, the speakers 250, 252 may be disposed on top of the first layer 260, as illustrated in FIG. 7, or they may be disposed between the first and second layers 260, 262 or the second 262 and third 264 layers. Having the speakers 250, 252 between layers may add to the comfort of the user so that a rigid speaker would not press directly against the user's ear. However, disposing the speakers 250, 252 on top of the first layer 260 may result in clearer sound transmission between the speakers 250, 252 and the user's ears.

Likewise, the position of resonant actuator 254 within the sling 200 may vary, but as illustrated in FIG. 7, the resonant actuator 254 is placed between the base cushion 232 and the first layer 260. The control module 256 may be positioned between the second layer 262 and third layer 264, as depicted in FIG. 7, with portions of the control module 256 accessible through the third layer 264. Thus, the first 260, second 262, and third 264 layers may provide surfaces onto which the various components may be disposed and/or secured, while providing comfortable barriers between the various components and the head and neck of the user.

Additionally, cutouts may be provided within the various layers to allow the cushions 238, 240, 242, control module 256, and electrical connections 266 to transverse layers and or provide the user with accessibility to the various components described herein. For example, in an embodiment where the control module 256 may be disposed between the second 262 and third 264 layers, and the speakers 250, 252 are disposed between the first 260 and second 262 layers, the electrical connections 266 connecting the control module 256 to the speakers 250, 252 may need to pass through the second layer 262. Also, for example, the first layer 260 may have one or more cutouts therein to allow the cushions 238, 240, 242 to be secured to the structural second layer 262 and pass through the first layer 260 to make contact with the user's head and neck during use. Also, cutouts in the third layer 264 may provide the control module 256 to be disposed between the second 262 and third 264 layers while being accessible to the user through the third layer 264. It will be appreciated that any of the layers may comprise one or more cutouts to allow for advantageous positioning of the various components integrated into the sling 200 described herein.

FIG. 9 further shows an embodiment of a strap 230 that may be incorporated into the embodiment of the sling 200 illustrated in FIGS. 6-8 or any of the other embodiments described herein. The strap 230 may be similar to the strap 130 illustrated in FIG. 5, except that it includes attachment members 226, 228 comprising loops of material rather than the D-rings illustrated in FIG. 5. The strap 230 between the attachment members 226, 228 may be made of the same material as the loops of the attachment members 226, 228. In at least one other embodiment, the attachment members 226, 228 may be made of different material than that of the strap 230. Also, in the illustrated embodiment, the strap 230 may be integrated into the sling 200 between the first 260 and second 262 layers. In other embodiments, particularly those embodiments having multiple layers as described herein, the strap 230 may be disposed between the second 262 and third 264 layers. In yet other embodiments, the strap 230 may be disposed on top of the first layer 260 or below the third layer 264.

Figure 10:
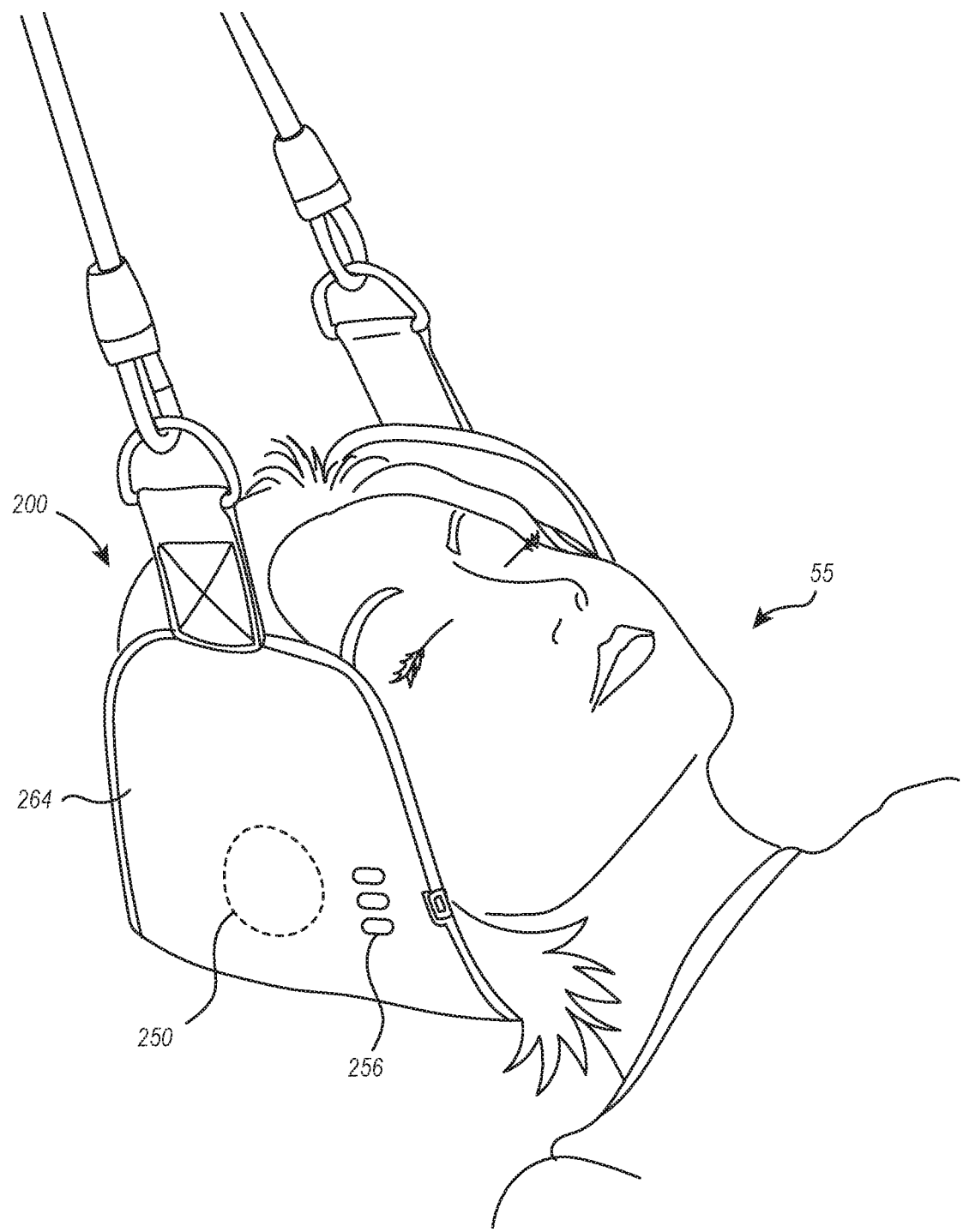
FIG. 10 illustrates a top perspective view of the traction device of FIG. 6 in use according to principles of the invention.

FIG. 10 illustrates an embodiment of a portable traction device that includes a sling 200 similar to the embodiment of the sling 200 illustrated in FIGS. 6-9. In particular, the sling 200 of FIG. 10 is shown as having at least one speaker 250 and a control module 256 accessible by the user during use. The speaker 250 corresponds in position to the user's right ear while the user's head 55 is positioned in the sling. As shown in FIGS. 6-10, a second speaker 252 may also correspond in position with the user's left ear while in use. Also, while not shown in FIG. 10, a resonant actuator 254 may be positioned to vibrate and massage the user's cervical muscles.

Also, as noted above, the sling 200 shown in FIG. 10 includes a control module 256 that is accessible to the user through the back side 258 of the sling 200. In particular, the control module 256, or at least a portion thereof, may be accessible through the third layer 264 of the sling 200. In this embodiment, the user can push various buttons or manipulate the control module 256, or buttons thereon, in order to adjust the volume of the speakers 250, 252, change songs, or adjust the vibrational intensity or modes of the resonant actuator 254.

It is further noted that the various features and aspects of the embodiment of the sling 200 illustrated in FIGS. 7-10 can be incorporated into the other embodiments described herein, such as embodiments shown in FIGS. 1-5, 16, and 19.

Figure 11:
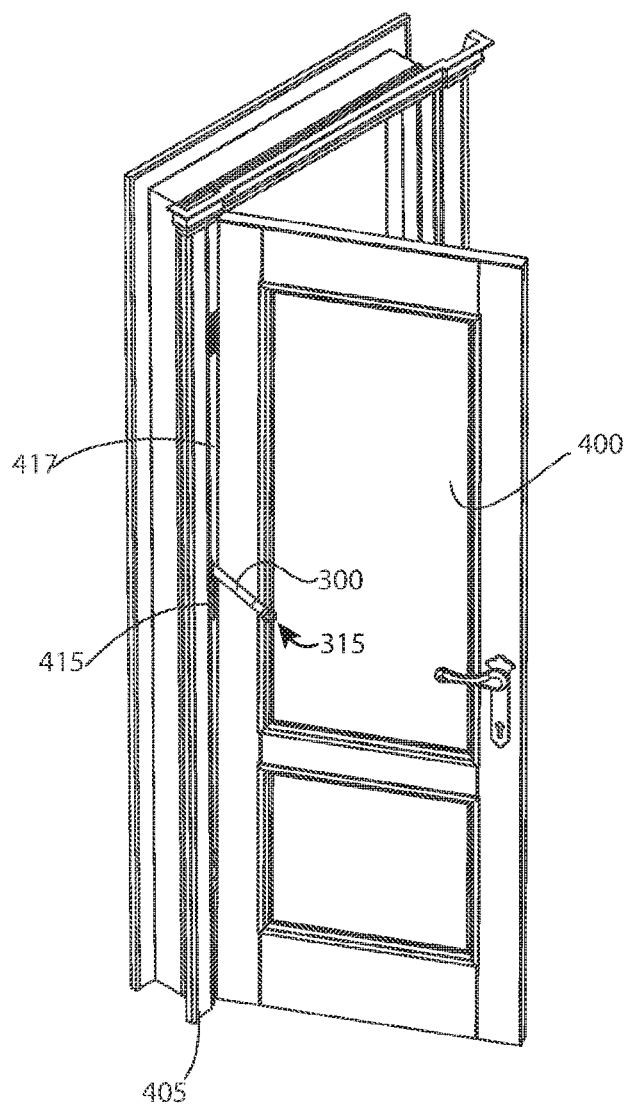
FIG. 11 illustrates a top perspective view of an exemplary anchor, in use, for a traction device according to principles of the invention.

In an exemplary embodiment, an anchor 300 is attached to a door 400 between the hinged side of the door 400 and the door frame 405. When the door 400 is opened, as shown in FIG. 11, an anchor tab 315 of the anchor 300 is slipped through the space 417 exposed between the hinged edge of the door 400 and the door frame 405, at a desired height. When the door 400 is closed, the space 417 is reduced or eliminated to prevent dislodging the anchor tab 315.

With reference to FIGS. 12-14, an exemplary anchor 300 for a traction device is illustrated. The anchor 300 includes a flexible strap 310 (e.g., nylon webbing) with an attachment 305 (e.g., D-ring) at one end, and an anchor tab 315 at the opposite end. The anchor tab 315 is sized to fit through the space exposed between the hinged edge of a door (e.g., door 400) and a door frame (e.g., door frame 405), when the door is open. However, the anchor tab 315 is thick enough to resist withdrawal through the space when the door is closed. For example, the anchor tab 315 can include a plastic tab of 0.1 to 1 inch (preferably about 0.5 inches) in thickness, folded and sewn layers of webbing with stitched seams, or other rigid structures including hardwood, metal, and composite prismatic polyhedron shaped tab-like structures of appropriate size to prevent the anchor tab from being pulled through the space when the door is closed. Additionally, the anchor tab 315 is firmly attached to the end of the strap 310 to prevent disconnection. The strap 310 is thin enough to allow closure of the door with the strap 310 between the hinged edge and frame of the door. While a D-ring 305 is illustrated for attachment to flexible elastic tethers 102, 104, other attachments such as carabiners, shackles, loops, spring clips, buckles and the like may be utilized within the scope of the invention.

Figure 15:
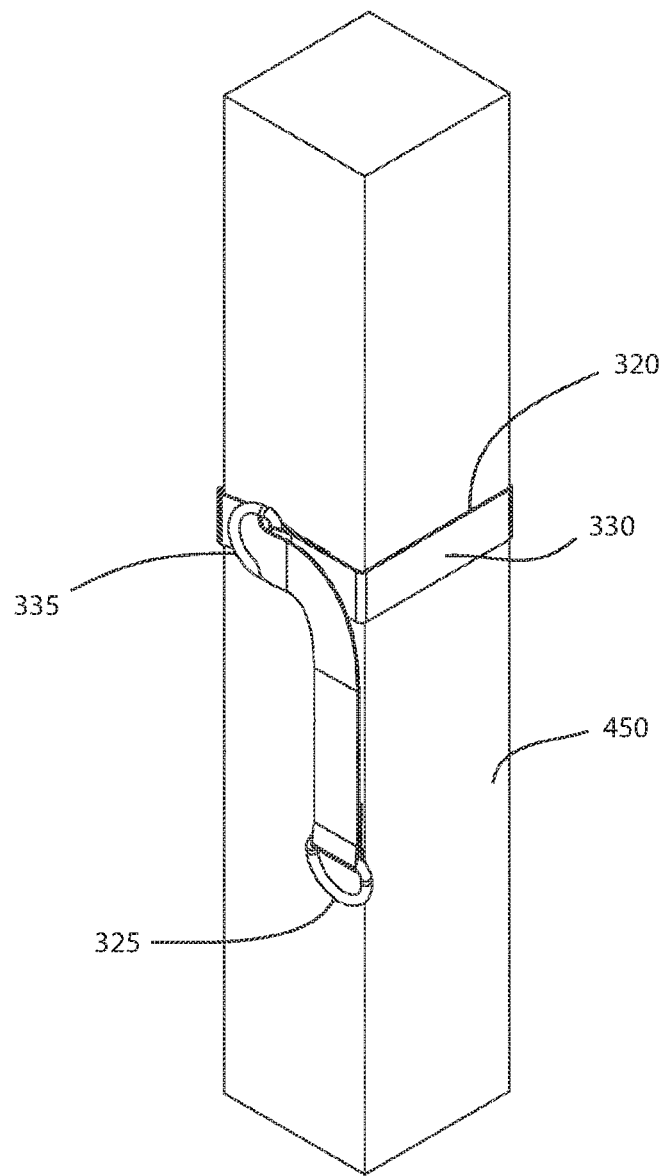
FIG. 15 illustrates a top perspective view of a leg anchor, in use, for a traction device according to principles of the invention.

Attachment to a door is preferred, as doors are ubiquitous, and this allows for portability and ease of use. However, an anchor may be attached to other structures such as a table leg 450 as illustrated in FIG. 15. In this embodiment, the anchor 320 includes a strap 330 with D-rings 325, 335 at each end, and a segment of the strap 330 threaded through one of the D-rings 355 to define a slip knot or noose surrounding the periphery of the leg 450 at a certain height. In such an implementation, one D-ring 355 may also serve as an anchor tab for use with a door.

Figure 16:
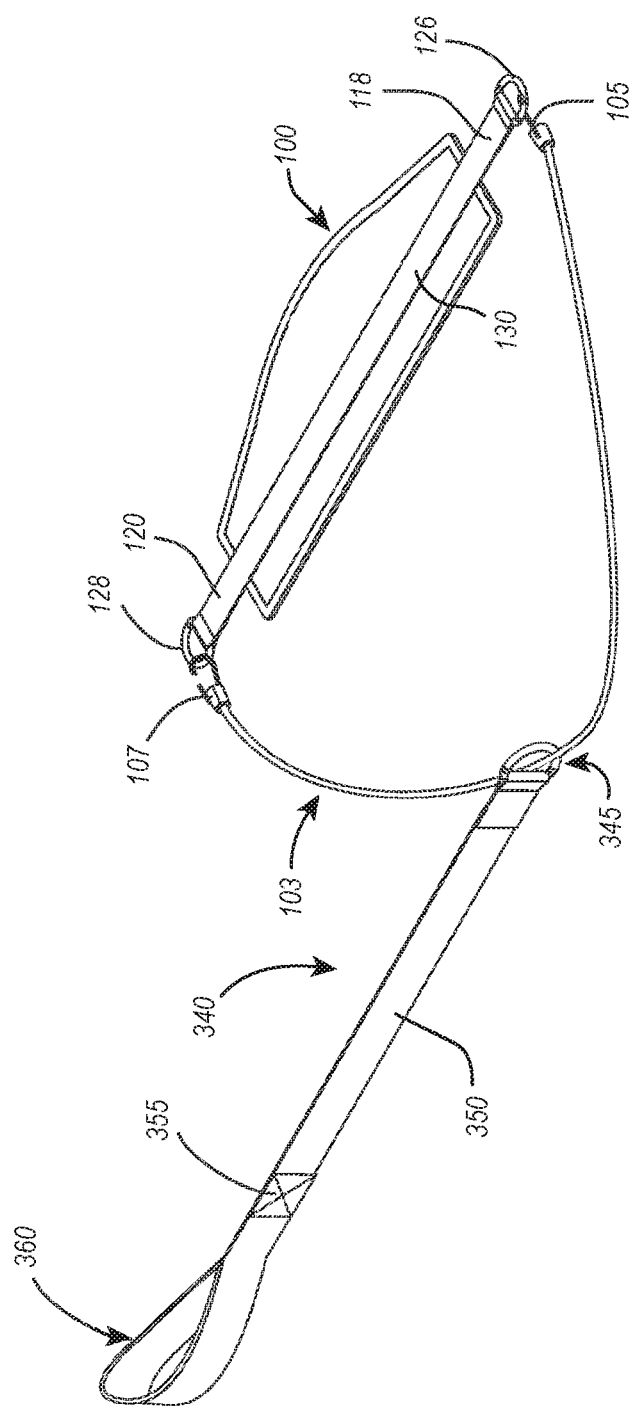
FIG. 16 illustrates a perspective view of an exemplary portable traction device according to principles of the invention.

Alternatively, an anchor 340 may include an anchor connector 345 at one end and a loop 360 at the other end, as shown, for example, in FIG. 16. The loop 360 may function similar to the D-ring attachment connector 335 illustrated in the embodiment shown in FIG. 15. That is, a segment of the strap 350 can be threaded through the loop 360 to define a slip knot or noose surrounding the periphery of a leg 450 or railing. The loop 360 of the anchor 340 illustrated in FIG. 16 may include a portion of the strap 350 folded over and sewn onto itself. The location where the loop is sewn may include an anchor tab 355. The anchor tab 355 may be thicker than other portions of the strap 350 due to multiple layers of the strap 350 sewn together, as well as the thread or adhesive materials used to secure the strap 350 to itself. The anchor tab 355 may therefore serve the same purpose as other anchor tabs described herein, for example the anchor tab 315 illustrated in FIGS. 12-14 and described above. Thus, the anchor of FIG. 16 can serve to secure a traction device both between a door and a doorframe and to a leg or railing.

FIG. 16 also illustrates how the anchor 340 may be secured to a sling 100. In the illustrated embodiment, the sling includes a single elastic tether 103 connected to respective side attachments 120, 118 of the sling at both ends 107, 105 of the elastic tether 103. The elastic tether 103 is threaded through the anchor connector 345 of the anchor 340. In this way, during use, the anchor 340 transfers the tensile force to the user's head through the elastic tether 103 to the sling 100, to produce traction of the user's neck, as described above. According to the illustrated embodiment, only a single elastic tether 103 is necessary, which reduces the complexity of the device and requires less parts for assembly.

Figure 17:
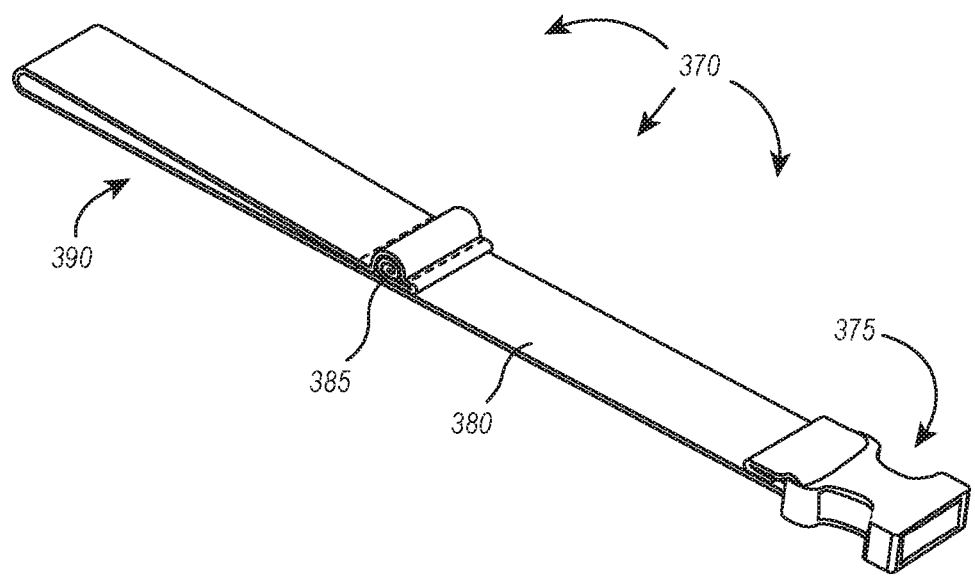
FIG. 17 illustrates a perspective view of an exemplary anchor according to principles of the invention.

Similarly, FIG. 17 illustrates an anchor 370 that includes a loop 390 and an anchor tab 385 including added material sewn back onto the strap 380. However, in the anchor 370 of FIG. 17, the anchor tab 385 includes material that has been rolled before being sewn to the strap 380 for added thickness of the anchor tab 385. Again, the anchor tab and loop may serve similar functions as those of the loop 360 and anchor tab 355 illustrated in FIG. 16. The anchor 370 illustrated in FIG. 17 also includes an anchor connector 375 that is a quick release connector. In the embodiment illustrated in FIG. 17, the quick release connector may be a female connector configured to releasably connect to a male quick release connector 510 as illustrated in FIG. 18.

Figure 18:
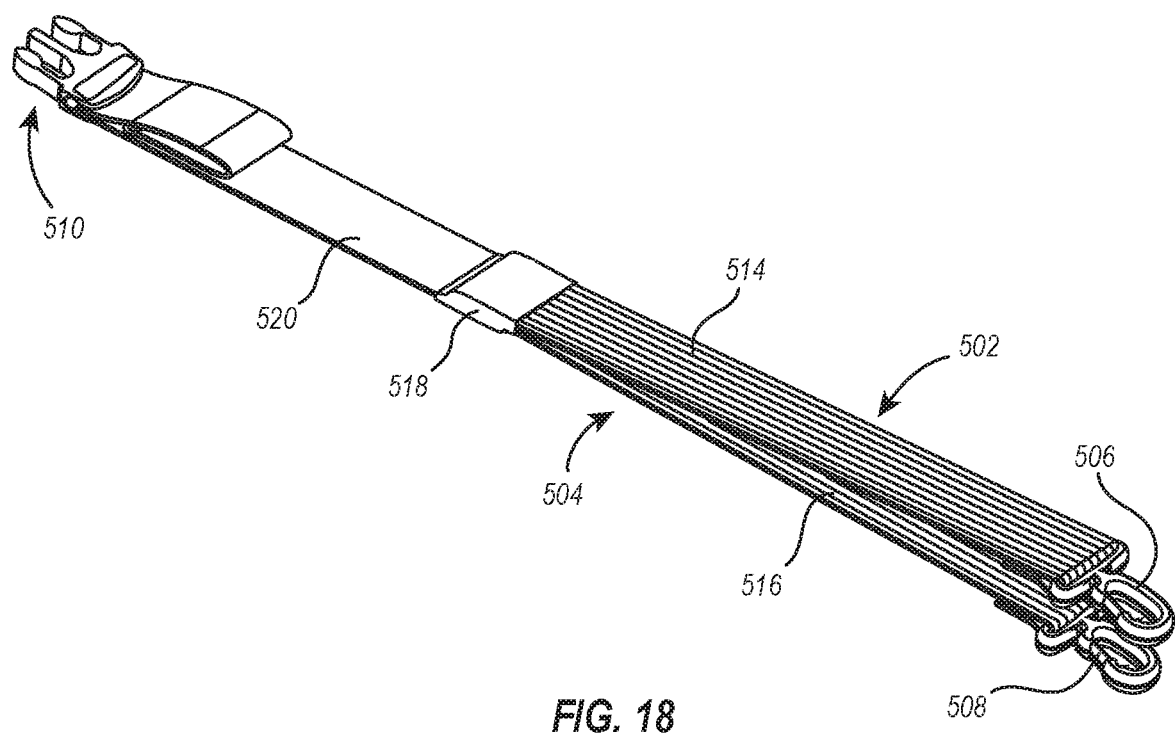
FIG. 18 illustrates a perspective view of an elastic tether according to principles of the invention.

FIG. 18 illustrates an embodiment of an elastic tether 504 that may be releasably connected to an anchor, such as the anchor 370 illustrated in FIG. 17. The elastic tether 504 is shown as having a male quick release connector 510 and an elastic portion 502 having two multi-strand elastic cords 514, 516. A strap portion 520 extends between the male quick release connector and an anchor tab 518. The anchor tab 518 may serve the same function as other anchor tabs described herein, and may also serve to connect the elastic portion 502 to the strap portion 520 of the elastic tether 504. The strap portion 502 includes two multi-strand elastic cords 514, 516 that connect to respective side attachments of a sling via hooks 506, 508. The multi-strand elastic cords 514, 516 are generally flat and planar, but in some embodiments, the multi-strand elastic cords may be stacked or bunched.

Figure 19:
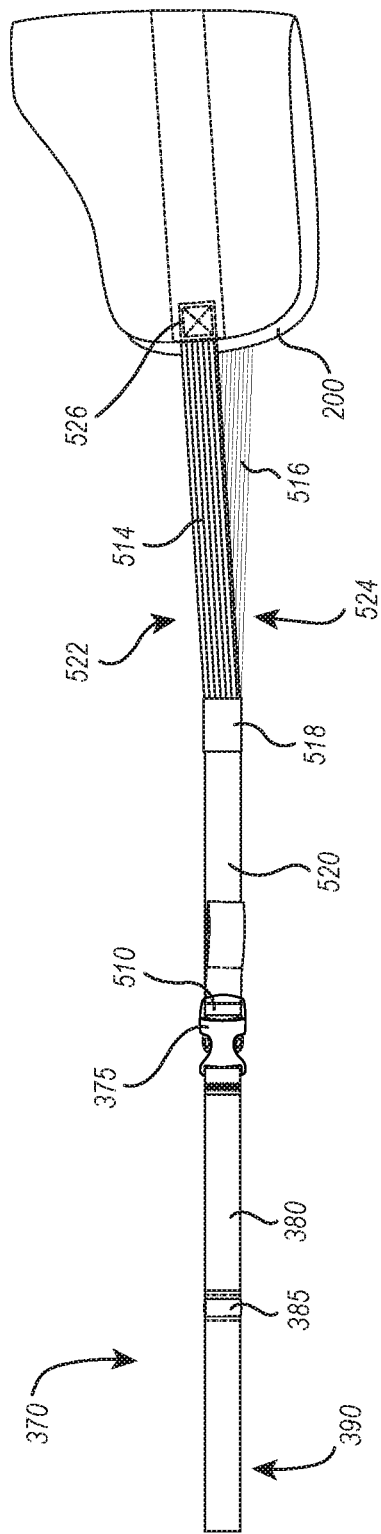
FIG. 19 illustrates a perspective view of an exemplary portable traction device according to principles of the invention.

Alternatively, the multi-strand elastic cords 514, 516 may be permanently secured to the sling 200, as illustrated in FIG. 19, at an attachment point 526. The multi-strand elastic cords 514, 516 may be secured to the sling 200 at the attachment point 526 by sewing, adhesives, or other attachments means. FIG. 19 illustrates the anchor 370 of FIG. 17 secured to an elastic tether 524 having an elastic portion 522 made up of two separate multi-strand elastic cords 514, 516 similar to the multi-strand elastic cords 514, 516 illustrated in FIG. 18. The multi-strand elastic cords 514, 516, being generally planar and having a width, may distribute the tensile force evenly across the sling 200, as far as the width of the cords 524, 526 provides and advantageously allow for improved cervical traction.

It will be appreciated that in some embodiments, the anchor 370 may include a male connector 375 and the elastic tether 524 may include the female end of the connector 510. Also, other embodiments may include other releasable connectors known in the art to serve the same purpose as the releasable connectors described herein.

The assembly illustrated in FIG. 19 allows a user to quickly clip and unclip the sling to an anchor 370 that has been secured through a door or around a leg or railing as described above. The user may not even need to remove the anchor 370 between uses. Instead, the user can simply unclip the sling 200 from the anchor 370 and leave the anchor secured in place so that when the user wants to use the device again there is no need to re-secure the anchor 370 to an anchoring object. This embodiment thus illustrates a portable traction device that include only two separate pieces and requires a single clip to fully assemble for use, greatly increasing the ease of setup and use and embodying a streamlined, portable cervical traction device that is comfortable and effective.

It should be appreciated that although the embodiments of FIGS. 18 and 19 disclose a pair of multi-strand elastic cords with one multi-elastic cord attached or configured to attach to opposing sides of the sling, embodiments including three or more (multi-strand) elastic cords are envisioned within the scope of this disclosure. For example, the portable traction device illustrated in FIG. 19 can additionally include a multi-strand elastic cord or other flexible elastic tether, as described herein, attached to the superior edge of the sling at a first end and associated with the anchor at the second end thereof. The second end can alternatively be associated with the pair of multi-strand elastic cords at the anchor tab.

While an exemplary embodiment of the invention has been described, it should be apparent that modifications and variations thereto are possible, all of which fall within the true spirit and scope of the invention. With respect to the above description then, it is to be realized that the optimum relationships for the components and steps of the invention, including variations in order, form, content, function and manner of operation, are deemed readily apparent and obvious to one skilled in the art, and all equivalent relationships to those illustrated in the drawings and described in the specification are intended to be encompassed by the present invention. The above description and drawings are illustrative of modifications that can be made without departing from the present invention, the scope of which is to be limited only by the following claims. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents are intended to fall within the scope of the invention as claimed.

What is claimed is:

1. A portable traction device for providing cervical traction to a user in a supine position, the portable traction device comprising:
    an elongated sling comprising flexible material and sized to cradle and engage a user's head when a first side of the elongated sling extends to a first side of the user's head and a second side of the elongated sling extends to a second side of the user's head while the portable traction device is in use;
    a resonant actuator integrated into the elongated sling;
    an anchor comprising a strap extending between an anchor tab and an anchor connector; and
    an elastic portion having a first end associated with the elongated sling and a second end associated with the anchor connector,
    wherein the elastic portion is strained and at an acute angle relative to a floor while the portable traction device is in use, the strained elastic portion producing a tensile force in a direction of the acute angle.

2. The portable traction device of claim 1, wherein the elongated sling comprises an inner first layer, a structural second layer, and an exterior third layer, the inner first layer and the exterior third layer comprising flexible fabric and the structural second layer comprising a flexible cushioning material disposed between the inner first layer and the exterior third layer.

3. The portable traction device as in claim 1, further comprising a base cushion attached to the elongated sling between a superior edge and an inferior edge thereof.

4. The portable traction device as in claim 3, further comprising a first side cushion and a second side cushion disposed on opposite sides of the base cushion.

5. The portable traction device as in claim 1, further comprising a speaker integrated into the elongated sling, wherein the speaker is positioned at or near an ear of the user while the portable traction device is in use.

6. The portable traction device as in claim 5, wherein the resonant actuator is positioned within the elongated sling at or near the occipital bone portion of the user's head while the portable traction device is in use.

7. The portable traction device as in claim 6, further comprising a control module having user input controls accessible on or through an exterior third layer of the elongated sling, wherein the control module is wired to the speaker and the resonant actuator, and wherein the user can manipulate the control module to at least adjust a volume of the speaker or adjust a vibrational intensity of the resonant actuator.

8. The portable traction device of claim 1, wherein the elastic portion comprises one or more flexible elastic tethers associated with opposite sides of the elongated sling.

9. The portable traction device as in claim 1, wherein the elastic portion comprises shock cords.

10. The portable traction device as in claim 1, wherein a superior edge of the elongated sling is arcuate.

11. A method of applying cervical traction comprising:
providing the portable traction device as in claim 1;
attaching the anchor of the portable traction device to an anchoring object at a height above a floor;
stretching the elastic portion to produce a tensile force having a horizontal vector component towards the anchor and a vertical vector component perpendicular to the horizontal component and upward away from the portable traction device; and
cradling a head of a substantially supine user within the sling while the elastic portion is stretched, wherein the substantially supine user's feet are positioned in a direction substantially opposite the horizontal vector component.

12. The method of claim 11, further comprising activating the resonant actuator disposed within the portable traction device.

13. The method of claim 11, further comprising activating one or more speakers disposed within the portable traction device.

14. A cervical traction system comprising:
a sling extending between first and second ends and configured to cradle a user's head during use;
an elastic portion associated with the first and second ends of the sling;
an anchor connector associated with the elastic portion; and
an anchor comprising a strap and a complementary anchor connector affixed to the strap, the complementary anchor connector configured to selectively engage the anchor connector of the elastic portion,
wherein the elastic portion is strained and at an acute angle relative to a floor while the cervical traction system is in use, the strained elastic portion producing a tensile force in a direction of the acute angle.

15. The cervical traction system of claim 14, wherein the elastic portion is associated with the first and second ends of the sling via a sling connector.

16. The cervical traction system of claim 15, further comprising one or more straps associated the first and second ends of the sling and configured to secure the sling to the sling connector.

17. The cervical traction system of claim 14, wherein the elastic portion is secured to the first and second ends of the sling at respective attachment points.

18. The cervical traction system of claim 14, further comprising a base cushion disposed centrally between the first and second ends of the sling and a resonant actuator associated with the base cushion.

19. The cervical traction system of claim 14, further comprising a pair of speakers connected to the sling, wherein the pair of speakers are positioned at or near respective ears of a user while the cervical traction system is in use.

* * * * *